United States Patent [19]

Bobbitt et al.

[11] Patent Number: 5,298,427
[45] Date of Patent: Mar. 29, 1994

[54] CHEMILUMINESCENT DETECTION OF AMINO ACIDS

[75] Inventors: Donald R. Bobbitt; Stephen N. Brune, both of Fayetteville, Ark.

[73] Assignee: The Board of Trustees of the University of Arkansas, Little Rock, Ark.

[21] Appl. No.: 922,004

[22] Filed: Aug. 4, 1992

Related U.S. Application Data

[63] Continuation of Ser. No. 513,753, Apr. 24, 1990, abandoned.

[51] Int. Cl.$^5$ .................... G01N 33/68; G01N 33/52; G01N 21/75; G01N 21/76
[52] U.S. Cl. ........................................ 436/89; 436/86; 436/90; 436/111; 436/166; 436/172
[58] Field of Search .................... 436/86–90, 436/111, 166, 172

[56] References Cited

U.S. PATENT DOCUMENTS

| | | | |
|---|---|---|---|
| 4,419,452 | 12/1983 | Imai et al. | 436/89 |
| 4,758,520 | 7/1988 | Matuszewski et al. | 436/89 X |
| 4,891,323 | 1/1990 | Stobaugh et al. | 436/89 X |
| 4,892,383 | 1/1990 | Klainer et al. | 436/165 X |

FOREIGN PATENT DOCUMENTS

1218947 9/1986 Japan.
8602734 5/1986 World Int. Prop. O.

OTHER PUBLICATIONS

Ege, D. et al., "Electrogenerated Chemiluminscent Determination of Ru(bpy)$_3{}^{2+}$at Low Levels" Analytical Chemistry, 56, 2413–2417, (1984).
Rubinstein, I. et al., "Electrogenerated Chemiluminscent Determination of Oxalate" Analytical Chemistry, 55, 1580–1582, (1983).
Miyaguchi, K. et al. "Sub-Picomole Chemiluminescence Detection of Dns-Amino Acids Separated by High-Performance Liquid Chromatography With Gradient Elution" Journal of Chromatography, 303, 173–177, (1984).
Analytical Chemistry, vol. 51, No. 11 Sep. 1979, pp. 1667–1674 "High Performance Liquid Chromatographic Determination of Subpicomole Amounts of Amino Acids by Precolumn Fluorescence Derivatization with o-Phthaldialdehyde".
Analytical Chemistry, vol. 59, No. 6 Mar. 15, 1967, pp. 865–868, "Generation of Chemiluminescence Upon Reaction of Aliphatic Amines With Tris (2,2'-bipyridine) ruthenium (III)".
Journal of the American Chemical Society 95:20, Oct. 3, 1973, pp. 6382–6589, "Electrogenerated Chemiluminescence. XIII. Electrochemical and Electrogenerated Chemiluminescence Studies of Ruthenium Chelates".
Journal of American Chemical Society, 1981, 103, pp. 512–516 "Electrogenerated Chemiluminescence. 37. Aqueous Ecl Systems Based on Ru(2,2'-bipyridine)$_3{}^{2+}$ and Oxalate or Organic Acids".
"Effect of pH on the Reaction of Tris(2,2'-bipyridly) ruthenium(III) with Amino Acids: Implications for Detection" Stephen N. Brune and Donald R. Bobbitt. Mikrochim. Acta[Wien] 1987, II, 79–90 "Luminol Chemiluminescence HPLC Reaction Detector for Amino Acids and Other Ligands" by Springer-Verlag 1988.

(List continued on next page.)

Primary Examiner—James C. Housel
Assistant Examiner—Rachel Heather Freed
Attorney, Agent, or Firm—Hermann Invester

[57] ABSTRACT

A detection system for determining the quantity of amino acid in a sample stream is provided based on the reaction of a buffer at a pH level from 10 to 11, with a reagent Ru(bpy)$_3{}^{3+}$, which is generated electrochemically on site. The detection system is further characterized by immediate luminescence upon reaction of the buffer in the pH range containing amino acid, with the reagent Ru(bpy)$_3{}^{3+}$. The detection system is capable of not only immediate detection of the quantity of amino acid in a sample stream, but even in very low concentrations.

6 Claims, 5 Drawing Sheets

OTHER PUBLICATIONS

Journal of Chromatography, 328 (1985) 121-126 Elsevier Science Publishers B. V., Amsterdam "Chemiluminsecence HPLC using ABEI".

Journal of Chromatography 440 (1988) 217-223 Elsevier Science Publishers B. V., Amsterdam. "Stereoselective Determination of L-Amino Acids Using Column Liquid Chromatography With . . . ".

Journal of Chromatography, 196 (1980) 319-322 Elsevier Scientific Publishing Company. "Fast determination of free amino acids by ion-pair high-performance liquid chromatography using on-line post-column derivitization".

Analytical Letters 19(23 & 24), 2277-2283 (1986) "A Chemiluminescent Precolumn Labelling Reagent for High-Performance Liquid Chromatography of Amino Acids".

CHEMILUMINESCENT DETECTION OF AMINO ACIDS

This is a continuation of application Ser. No. 07/513,753, filed Apr. 24, 1990 now abandoned.

FIELD OF THE INVENTION

The present invention relates to a chemiluminescent detection system of the type suitable for generating luminosity indicative of the quantity of amino acid in a sample stream.

BACKGROUND OF THE INVENTION

A sample stream containing amino acid may be the effluent of a high performance liquid chromatography system or a flow injection analysis system. Once a sample stream is obtained, the amino acid may be converted by derivitization. Detecting the quantity of amino acid present has then been achieved by either spectrophotometric absorption or fluorescence spectroscopy.

The derivitization process is both time consuming and complex. Efforts to eliminate the need for conversion of the amino acid have resulted in the use of the reagent Tris(2,2'-bipyridyl)ruthenium(III) (sometimes referred to herein as $Ru(bpy)_3^{3+}$), which may be generated on site, resulting in immediate luminescence when merged with amino acids in a buffered solution of a specified pH range.

SUMMARY OF THE INVENTION

The present invention provides a detection system for amino acids in volumes >1 microliter by the use of an electrochemically generated reagent to produce immediate luminescence when merged with amino acids in a buffered solution of a specified pH range.

The above object is achieved by merging the electrochemically generated $Ru(bpy)_3^{3+}$ with a sample stream of amino acid, buffered at a pH in the range of 10–11. As the reaction occurs with facility above pKa of the amino acid, the presence of amino acid in the sample stream when merged with the reagent $Ru(bpy)_3^{3+}$ results in luminescence, which may be detected by a photomultiplier tube. The measured emissions are indicative of the quantity of amino acid present in the sample stream.

Thus, a detection system appropriates for volumes <1 microliter which allows for on-site electrochemical generation of $Ru(bpy)_3^{3+}$, and which results in spontaneous luminescence in the presence of amino acid, has been achieved.

DESCRIPTION OF THE PREFERRED EMBODIMENTS

Figure 1:
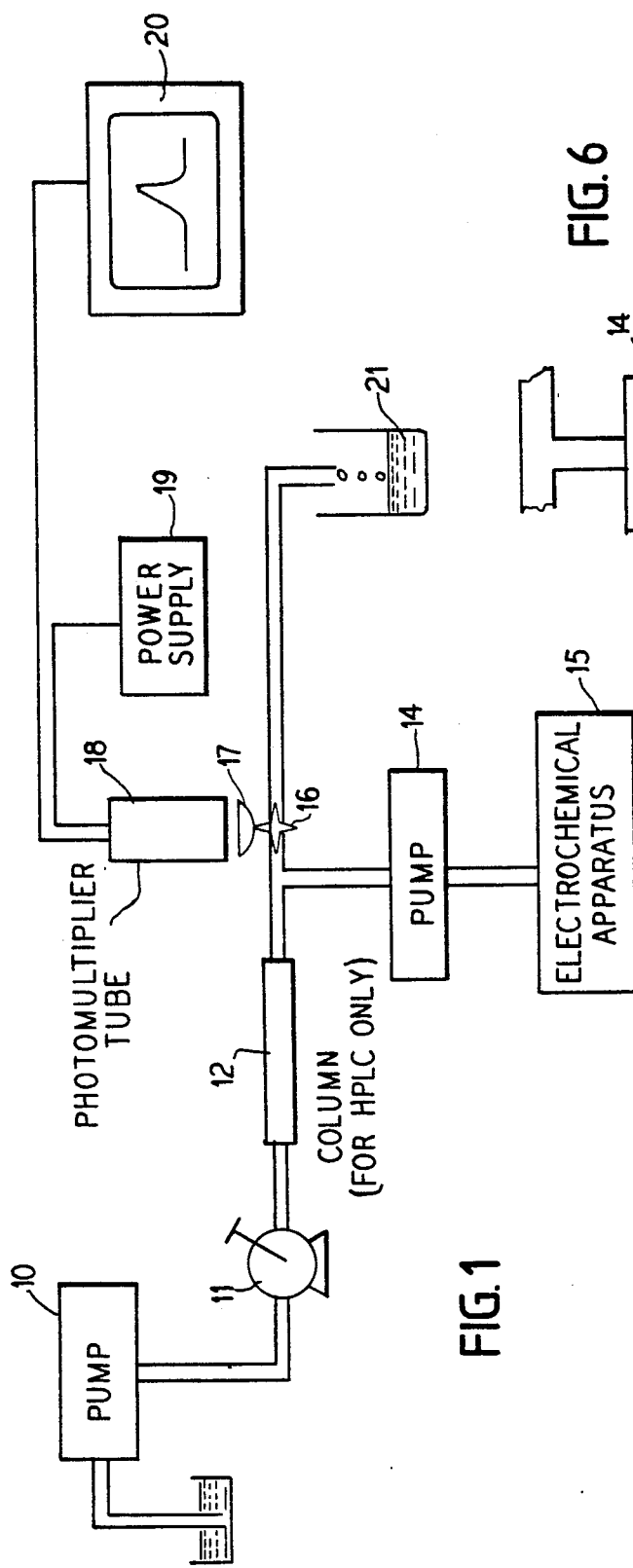
FIG. 1 is a schematic representation of the detection system provided in accordance with this invention.

FIG. 1 is a schematic representation of the detection system. A pump 10 is used at a first point in the circuit to establish a flow rate for the buffer. At a second point in the circuit, a valve 11 is switched, introducing a sample to the buffer which proceeds through a high performance liquid chromatography system, in which the amino acids are separated out into a column 12, the end of which is connected to a glass or plastic tube 13. Therein, the buffer and a reagent 14, which has been electrochemically generated by a generating means 15 identified in FIG. 6 below, are merged, and flow into a concentric coil 16 from which the luminescent output is focused by a lens 17, causing photoemissions in a photomultiplier tube 18, where the potential across the dynode string is supplied by a high voltage power supply 19 at 1 KV. Any suitable buffer, such as a buffer consisting of $K_2HPO_4$, $H_3BO_3$, or $KH_2PO_4$, can be used in conjunction with the reagent 14. The resulting signal is displayed on a CRT 20. After passing through the concentric coil 16, the mixture flows to a waste container 21.

Figure 2:
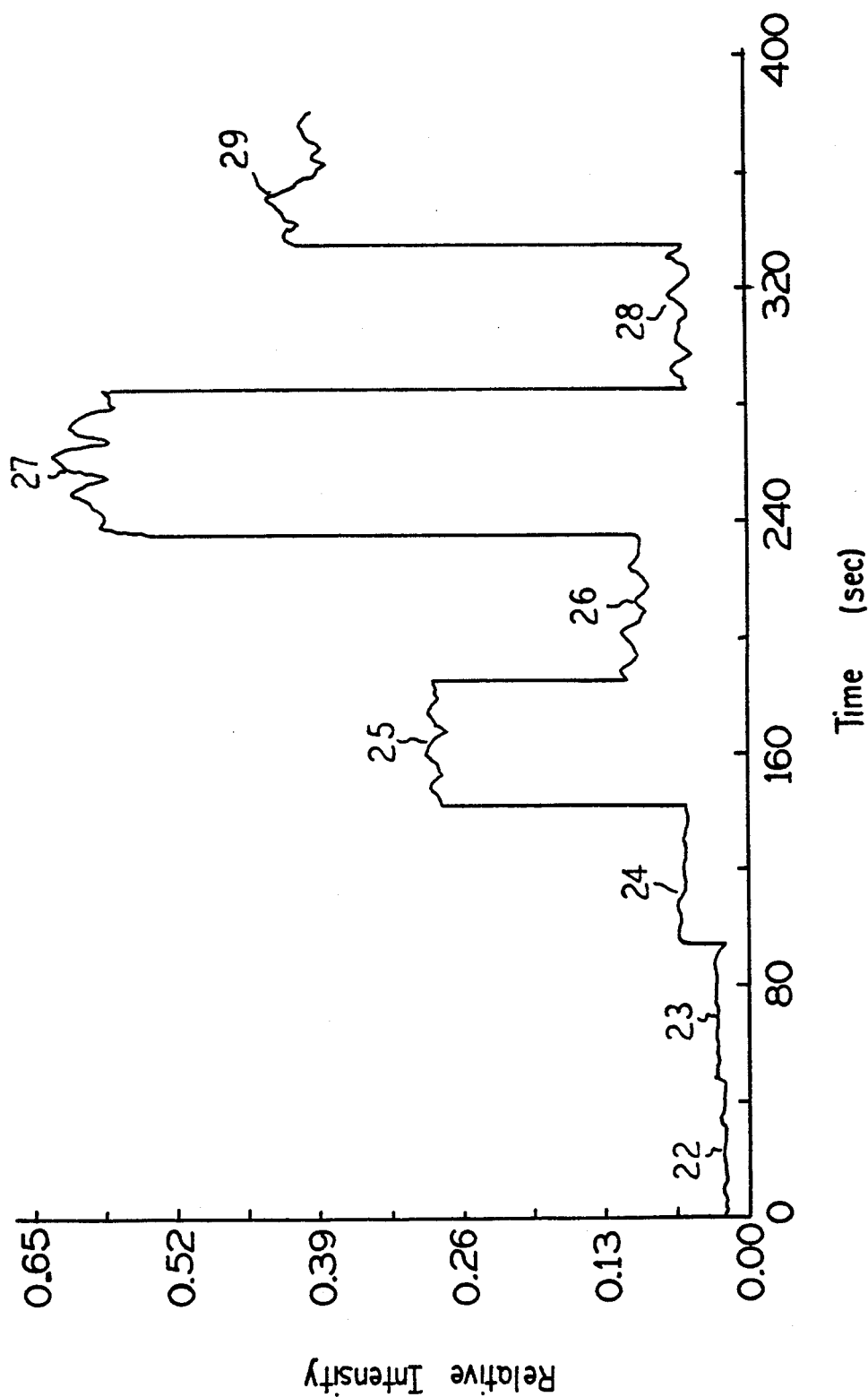
FIG. 2 illustrates the relative intensity of the luminescence for the $Ru(bpy)_3^{3+}$ reaction with an amino acid at various pH levels.

An illustration of the relative intensity of the output signal with respect to time is shown in FIG. 2. At 22, 24, 26, and 28, the relative intensity of the output signal with respect to time is demonstrated for the reaction of the reagent with a buffer, which does not contain amino acid, at pH levels of 8, 9, 10, and 11 respectively. At 23, 25, 27, and 29, the relative intensity of the output signal with respect to time is demonstrated for the reaction of the reagent with a buffer containing the amino acid glutamate at pH levels of 8, 9, 10, and 11 respectively.

Figure 3:
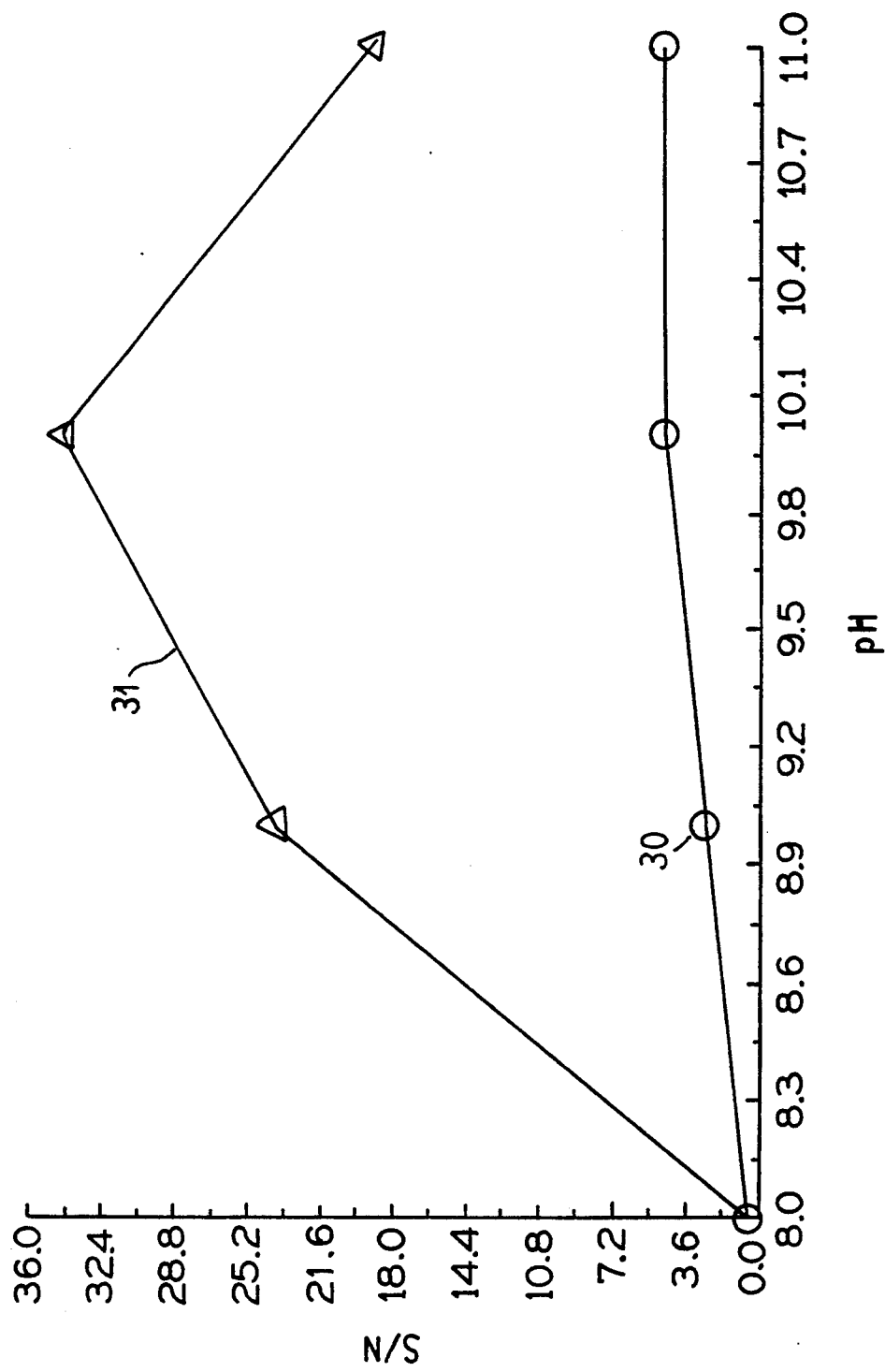
FIG. 3 is a graphical representation of the change in magnitude of the resulting signal for reactions where the pH levels are >pKa for valine and glutamate.

FIG. 3 is a plot of the experimental results of the detection system for the amino acids glutamate 30 and valine 31, demonstrating the increase in the detected signal at pH levels >pKa of the amino acid.

Figure 4:
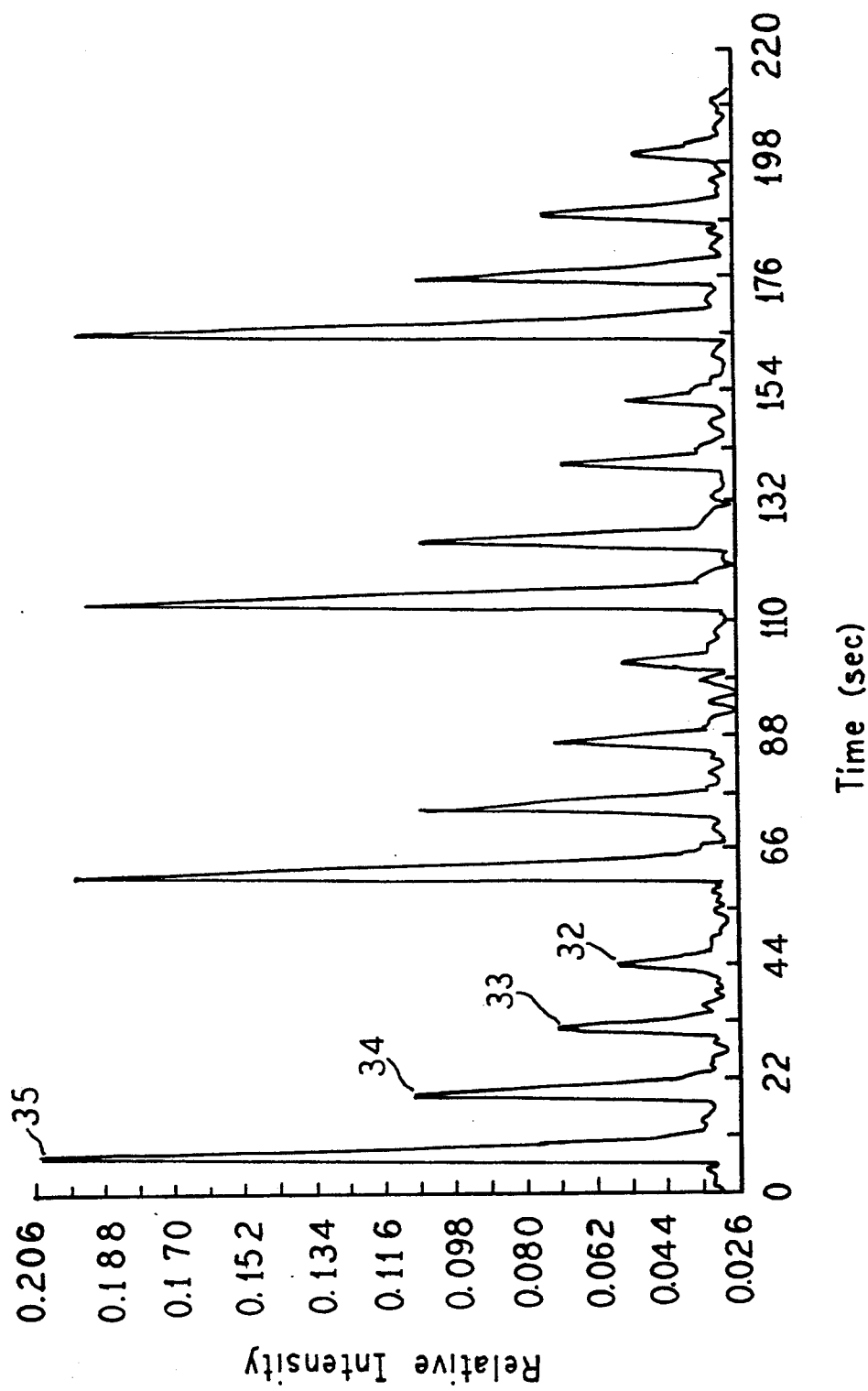
FIG. 4 illustrates the variation of the output response of the system for varied concentrations of methionine.

The system response to concentrations of 0.05 mM 32, 0.1 mM 33, 0.2 mM 34, and 0.5 mM 35, of methionine is illustrated in FIG. 4, where the $Ru(bpy)_3^{3+}$ concentration is 1.5 mM.

Figure 5:
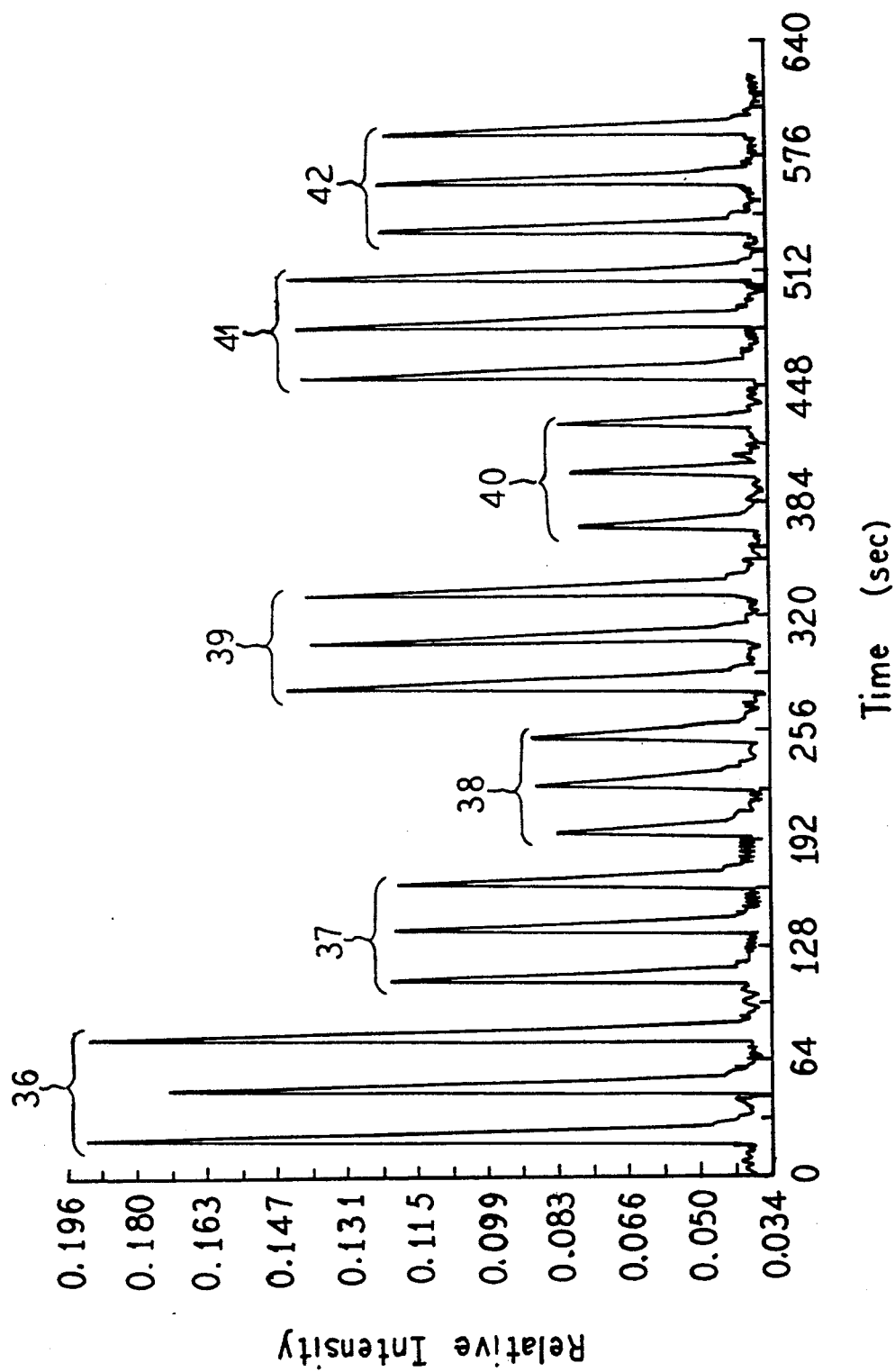
FIG. 5 illustrates the output response of six different amino acids at 0.1 mM concentration as merged with 1.5 mM $Ru(bpy)_3^{3+}$.

FIG. 5 illustrates the system response for six amino acids. Valine 36, glutamic acid 37, tryptophan 38, methionine 39, arginine 40, phenylalanine 41, and glutamic acid (control) 42, where tested at a concentration of 0.1 mM with the reagent $Ru(bpy)_3^{3+}$ at a concentration of 1.5 mM.

The following table gives the relative luminescence efficiency for the eight amino acids tested with the $Ru(bpy)_3^{3+}$ detection system.

| | Relative Luminosity/mole | | |
|---|---|---|---|
| Name | Sidechain Type | # in Category | Relative Luminescence/mole |
| THR | Alcohol | 3* | 1 |
| GLY | Hydrogen | 1 | 1.4 |
| ARG | Amine | 4 | 4.8 |
| TRP | Aromatic Amine | 2 | 6.4 |
| GLU | Acid | 2 | 9.8 |
| PHE | Aromatic | 2* | 11.5 |
| MET | Sulfer | 2 | 14.6 |
| VAL | Hydrocarbon | 5 | 17.1 |

*TYR overlap

Synthesis of Ru(bpy)$_3^{3+}$

Figure 6:
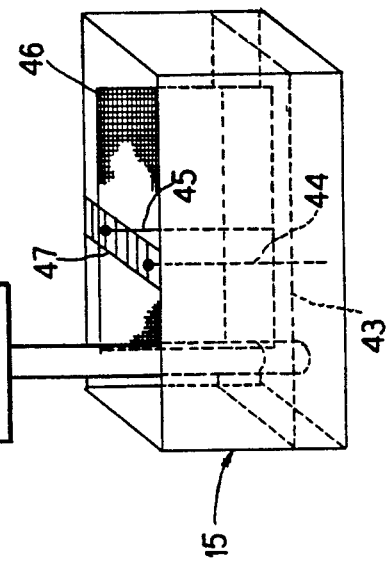
FIG. 6 is a schematic representation of the electrochemical generating means.

The apparatus which makes electrochemical generation of the reagent possible is schematically shown in FIG. 6. A working electrode, composed of a 6.25 cm$^2$ piece of platinum gauze 46, a pseudo-reference electrode, consisting of a silver wire 45, and an auxiliary electrode, consisting of a platinum wire 44, are immersed in a 0.4M sulfate electrolyte 43. The auxiliary electrode 44 is separated from the pseudo-reference 45 and working 46 electrodes by a porous glass frit 47. The working electrode 46 is maintained at a potential of 1.3 V with respect to the pseudo-reference electrode 45.

Synthesis of the Ru(bpy)$_3^{3+}$ is achieved by introducing 1.5 mM of Tris(2,2'-bipyridyl)ruthenium(II) (herein referred to as Ru(bpy)$_2^{2+}$ to the sulfate electrolyte 43. The ensuing reaction in the presence of a 1.3 V potential difference across the working 46 and pseudo-reference 45 electrodes results in the electrochemical oxidation of Ru(bpy)$_2^{2+}$, which yields Ru(bpy)$_3^{3+}$. The reagent can now be extracted employing a pump 14 for introduction to the sample stream containing amino acid.

Chemicals and Compositions Utilized

Amino acid samples were obtained from Sigma Chemical Co., with a stated purity of 99+%. Tris(2,2'-bipyridyl)ruthenium(II)chloride hexahydrate (#22,475-8) was purchased from Aldrich Chemical Co. All remaining buffers and solvents were purchased from Fischer Scientific, and were listed as Reagent Grade.

It will be understood that we wish to embody within the scope of the patent warranted hereon all such modifications as might be suggested by those versed in the art.

We claim as our invention:

1. The method of detecting amino acid in volumes >1 microliter in a stream which includes the steps of:
   (a) introducing a liquid sample in the form of a stream flowing through a circuit,
   (b) selectively establishing the flow rate of said stream by the use of a pump,
   (c) separating the amino acid from other constituents in said stream to form an amino acid stream,
   (d) buffering said amino acid stream to achieve a selected pH level, wherein said selected pH level ranges from pH 10 to pH 11,
   (e) electrochemically generating Ru(bpy)$_3^{3+}$ on site,
   (f) merging the Ru(bpy)$_3^{3+}$ with said buffered amino acid stream to produce immediate spontaneous luminescence in the presence of various concentrations of amino acid, and
   (g) photometrically measuring the quantity of amino acid present as a function of the luminescence.

2. A method as defined in claim 1, wherein said stream is a buffer consisting of K$_2$HPO$_4$.

3. A method as defined in claim 1, wherein said stream is a buffer consisting of H$_3$BO$_3$.

4. A method as defined in claim 1, wherein said stream is a buffer consisting of KH$_2$PO$_4$.

5. The method of detecting amino acids in volumes >1 microliter in a stream, which includes the steps of:
   (a) introducing a liquid sample in the form of a stream flowing through a circuit,
   (b) selectively establishing the flow rate of said stream by the use of a pump,
   (c) buffering said stream to form a buffered stream,
   (d) separating buffered amino acid from other constituents in said buffered stream to form a buffered amino acid stream, wherein said buffered amino acid stream is buffered to achieve a selected pH level, and wherein said selected pH level ranges from pH 10 to pH 11,
   (e) electrochemically generating Ru(bpy)$_3^{3+}$ on site,
   (f) merging the Ru(bpy)$_3^{3+}$ with said buffered amino acid stream to produce immediate spontaneous luminescence in the presence of various concentrations of amino acid, and
   (g) photometrically measuring the quantity of amino acid present as a function of the luminescence.

6. The method for chemiluminescent detection of amino acids via reaction with Ru(bpy)$_3^{3+}$ wherein light is produced as a product of the reaction in proportion to an amount of amino acid, which includes the steps of:
   (a) adjusting the pH level of a sample to be tested to a level of approximately pH 10,
   (b) introducing Ru(bpy)$_3^{3+}$ to said sample to produce a mixture, wherein introducing said Ru(bpy)$_3^{3+}$ to said sample results in the immediate luminescence of said mixture at said level, and
   (c) measuring the luminescence as a function of the amount of amino acid present.

* * * * *